United States Patent
Chono et al.

(10) Patent No.: US 12,198,393 B2
(45) Date of Patent: Jan. 14, 2025

(54) IMAGING SYSTEM, IMAGING METHOD, AND COMPUTER READABLE MEDIUM

(71) Applicant: NEC Corporation, Tokyo (JP)

(72) Inventors: Keiichi Chono, Tokyo (JP); Ryuichi Akashi, Tokyo (JP); Yuka Ogino, Tokyo (JP)

(73) Assignee: NEC CORPORATION, Tokyo (JP)

( * ) Notice: Subject to any disclaimer, the term of this patent is extended or adjusted under 35 U.S.C. 154(b) by 0 days.

(21) Appl. No.: 18/509,633

(22) Filed: Nov. 15, 2023

(65) Prior Publication Data

US 2024/0078780 A1    Mar. 7, 2024

Related U.S. Application Data

(63) Continuation of application No. 17/801,441, filed as application No. PCT/JP2020/008110 on Feb. 27, 2020.

(51) Int. Cl.
*G06V 10/141* (2022.01)
*G06V 40/18* (2022.01)
*G06V 40/19* (2022.01)

(52) U.S. Cl.
CPC .............. *G06V 10/141* (2022.01); *G06V 40/19* (2022.01); *G06V 40/197* (2022.01)

(58) Field of Classification Search
CPC ...................................................... G06V 10/141
See application file for complete search history.

(56) References Cited

U.S. PATENT DOCUMENTS

| | | | |
|---|---|---|---|
| 6,252,977 | B1 | 6/2001 | Salganicoff et al. |
| 10,176,563 | B2 * | 1/2019 | Kemp ..................... G06F 3/048 |
| 2005/0213796 | A1 | 9/2005 | Ikoma et al. |
| 2005/0248725 | A1 | 11/2005 | Ikoma et al. |
| 2009/0016574 | A1 | 1/2009 | Tsukahara |
| 2009/0237208 | A1 * | 9/2009 | Tsukahara .............. A61B 5/117 |
| | | | 340/5.82 |

FOREIGN PATENT DOCUMENTS

| | | |
|---|---|---|
| JP | H10-5195 A | 1/1998 |
| JP | 2003-308523 A | 10/2003 |
| JP | 2005-258860 A | 9/2005 |
| JP | 2005-304809 A | 11/2005 |
| JP | 2007-319174 A | 12/2007 |
| JP | 2007-319175 A | 12/2007 |
| WO | 2006/088042 A1 | 8/2006 |

OTHER PUBLICATIONS

International Search Report for PCT Application No. PCT/JP2020/008110, mailed on May 26, 2020.
Extended European Search Report for EP Application No. 20921992.2, dated on Jan. 5, 2023.

* cited by examiner

*Primary Examiner* — Edward Park
(74) *Attorney, Agent, or Firm* — Sughrue Mion, PLLC

(57) ABSTRACT

An imaging system (10) includes: iris imaging means (1) for photographing an iris of a subject; first irradiation means (2a) for applying light to the subject; and second irradiation means (2b) for applying light to the subject in such a manner that an angle between an optical axis of the light emitted from the second irradiation means (2b) and an optical axis of the iris imaging means (1) is larger than an angle between an optical axis of the light emitted from the first irradiation means (2a) and the optical axis of the iris imaging means (1).

9 Claims, 20 Drawing Sheets

IMAGING SYSTEM, IMAGING METHOD, AND COMPUTER READABLE MEDIUM

This application is a Continuation of U.S. application Ser. No. 17/801,441 filed on Aug. 22, 2022, which is a National Stage Entry of PCT/JP2020/008110 filed on Feb. 27, 2020, the contents of all of which are incorporated herein by reference, in their entirety.

TECHNICAL FIELD

This disclosure relates to an imaging system, an imaging method, and a computer readable medium suitable for acquiring an image used for iris authentication.

BACKGROUND ART

Biometric authentication using an iris(es) (i.e., iris authentication) has been known. In such biometric authentication, an iris(es) of a subject is photographed by using an imaging system, and feature values are extracted from the pattern(s) of the photographed iris(es). An iris, which is a doughnut-shaped tissue surrounding a pupil, has a very complex pattern and the pattern is unique to each individual person. This type of apparatus requires an image in which the iris of a subject is properly photographed (i.e., is properly shown).

Patent Literature 1 discloses an imaging system in which an image of an eyeball of a person is taken by applying light to the eyeball at one incident angle, and if it is determined that the taken image is not satisfactory, an image of the iris is taken again by applying light at an incident angle different from the one incident angle in a successive manner.

CITATION LIST

Patent Literature

Patent Literature 1: Japanese Unexamined Patent Application Publication No. H10-005195

SUMMARY OF INVENTION

Technical Problem

Incidentally, there are cases where a subject is wearing glasses or the like.

An object of this disclosure is to provide an imaging system, an imaging method, and a computer readable medium capable of solving the above-described problem.

Solution to Problem

An imaging system according to a first aspect of this disclosure includes: iris imaging means for photographing an iris of a subject; first irradiation means for applying light to the subject; and second irradiation means for applying light to the subject in such a manner that an angle between an optical axis of the light emitted from the second irradiation means and an optical axis of the iris imaging means is larger than an angle between an optical axis of the light emitted from the first irradiation means and the optical axis of the iris imaging means.

An imaging method according to a second aspect of this disclosure includes: a step of determining whether or not a subject is wearing a glass or the like; a step of, when it is determined that the subject is not wearing the glass or the like, applying light to the subject from first irradiation means; and a step of, when it is determined that the subject is wearing the glass or the like, applying light to the subject from second irradiation means, the second irradiation means being configured so that an angle between an optical axis of the light emitted from the second irradiation means and an optical axis of iris imaging means is larger than an angle between an optical axis of the light emitted from the first irradiation means and the optical axis of the iris imaging means, the iris imaging means being means for photographing an iris of the subject.

A non-transitory computer readable medium according to a third aspect of this disclosure stores a program for causing a computer to perform: a step of determining whether or not a subject is wearing a glass or the like; a step of, when it is determined that the subject is not wearing the glass or the like, applying light to the subject from first irradiation means; and a step of, when it is determined that the subject is wearing the glass or the like, applying light to the subject from second irradiation means, the second irradiation means being configured so that an angle between an optical axis of the light emitted from the second irradiation means and an optical axis of iris imaging means is larger than an angle between an optical axis of the light emitted from the first irradiation means and the optical axis of the iris imaging means, the iris imaging means being means for photographing an iris of the subject.

EXAMPLE EMBODIMENT

An example embodiment according to this disclosure will be described hereinafter with reference to the drawings. For clarifying the explanation, the following descriptions and the drawings are partially omitted and simplified as appropriate. Further, the same symbols are assigned to the same components/structures throughout the drawings, and redundant explanations thereof are omitted as appropriate.

First Example Embodiment

A first example embodiment will be described hereinafter.

Figure 1:
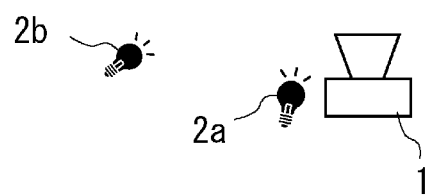
FIG. 1 is a block diagram showing a configuration of an imaging system according to a first example embodiment.

FIG. 1 is a block diagram showing a configuration of an imaging system 10 according to a first example embodiment. As shown in FIG. 1, the imaging system 10 includes an iris imaging device (iris imaging means) 1, first irradiation means (a first illuminator) 2a, and second irradiation means (a second illuminator) 2b.

The iris imaging device 1 is used to photograph an iris(es) of a subject. The first illuminator 2a is used to apply light to the subject. The second illuminator 2b is configured for applying light to the subject so that an angle between the optical axis of light emitted from the second illuminator 2b and the optical axis of the iris imaging means is larger than an angle between the optical axis of light emitted from the first illuminator 2a and the optical axis of the iris imaging device 1.

By using the above-described configuration, it is possible to obtain an image in which the iris(es) of the subject is properly photographed (i.e., is properly shown) irrespective of whether or not the subject is wearing glasses or the like.

Second Example Embodiment

A second example embodiment will be described hereinafter.

Figure 2:
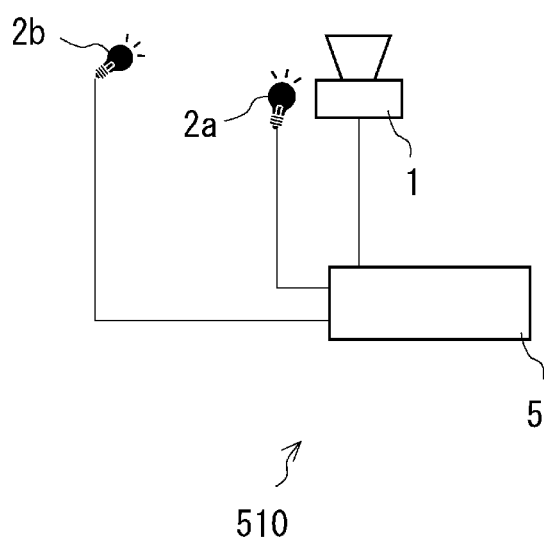
FIG. 2 is a block diagram showing a configuration of an imaging system according to a second example embodiment.

Firstly, an example of a configuration of an imaging system according to the second example embodiment will be described. FIG. 2 is a block diagram showing a configuration of an imaging system 510 according to the second example embodiment. As shown in FIG. 2, the imaging system 510 includes an iris imaging device 1, a first illuminator 2a, a second illuminator 2b, and a controller (control means) 5. That is, the imaging system 510 is different from the above-described imaging system 10 according to the first example embodiment (see FIG. 1) in that the imaging system 510 further includes the controller 5.

The controller 5 determines whether or not the subject is wearing glasses or the like, and controls the operations performed by the first and second illuminators 2a and 2b based on the result of the determination. Specifically, when the controller 5 determines that the subject is not wearing glasses or the like, the controller 5 operates the first illuminator 2a so that light is emitted from the first illuminator 2a. On the other hand, when the controller 5 determines that the subject is wearing glasses or the like, the controller 5 operates the second illuminator 2b so that light is emitted from the second illuminator 2b.

Figure 3:
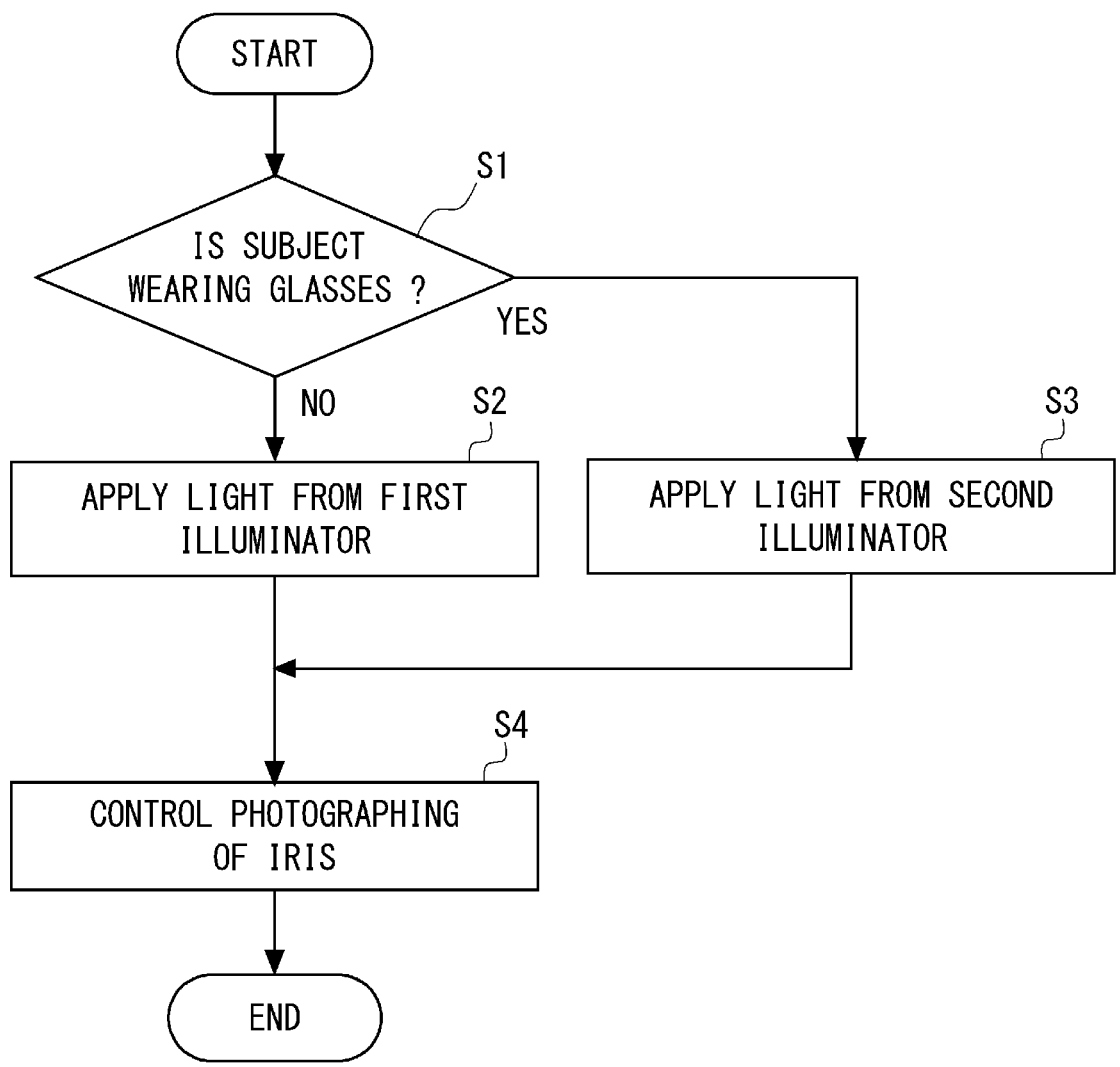
FIG. 3 is a flowchart for explaining a flow of an imaging process in the imaging system according to the second example embodiment.

FIG. 3 is a flowchart for explaining a flow of an imaging process performed in the imaging system 510. As shown in FIG. 3, firstly, the controller determines whether or not the subject is wearing glasses or the like (Step S1).

In the step S1, when the controller 5 determines that the subject is not wearing glasses or the like (No), the controller 5 operates the first illuminator 2a so that light is emitted from the first illuminator 2a (Step S2). In the step S1, when the controller 5 determines that the subject is wearing glasses or the like (Yes), the controller 5 operates the second illuminator 2b so that light is emitted from the second illuminator 2b (Step S3). Subsequent to the step S2 or S3, the controller 5 acquires a captured image of an iris(es) by controlling the iris imaging device 1 (Step S4). The captured image of the iris(es) acquired in the step S4 is used for iris authentication or registration.

As described above, the imaging system 510 includes the first illuminator 2a, and the second illuminator 2b which is configured so that the angle between the optical axis of light emitted from the second illuminator 2b and the optical axis of the iris imaging means is larger than the angle between the optical axis of light emitted from the first illuminator 2a and the optical axis of the iris imaging device 1. By emitting light from the second illuminator 2b when the subject is wearing glasses or the like, it is possible to prevent (or reduce) the reflected light from the glasses or the like from entering the iris imaging means 1. As a result, a possibility that a captured image acquired by the imaging system 510 is appropriate for iris authentication even when the subject is wearing glasses or the like is increased, thus making it possible, by performing iris authentication by using the above-described captured image, to improve the success rate of the iris authentication. As a result, the subject wearing the glasses or the like does not have to take off the glasses or the like, so that the convenience is improved.

On the other hand, when the subject is not wearing glasses or the like, light is emitted from the first illuminator 2a. The overlapping range between the irradiation range of the first illuminator 2a and the imaging range of the iris imaging device 1 is larger than the overlapping range between the irradiation range of the second illuminator 2b and the imaging range of the iris imaging device 1. The larger the overlapping range is, the higher the possibility that the acquired captured image of the iris(es) of the subject is appropriate for iris authentication becomes. When the subject is not wearing glasses or the like, there is no need to take the prevention (or the reduction) of the reflected light from the glasses or the like into consideration. Therefore, by emitting light from the first illuminator 2a of which the overlapping range with the imaging range of the iris imaging device 1 is large, the risk that the photographing needs to performed again is reduced, so that the convenience is improved.

Third Example Embodiment

A third example embodiment will be described hereinafter.

Figure 4:
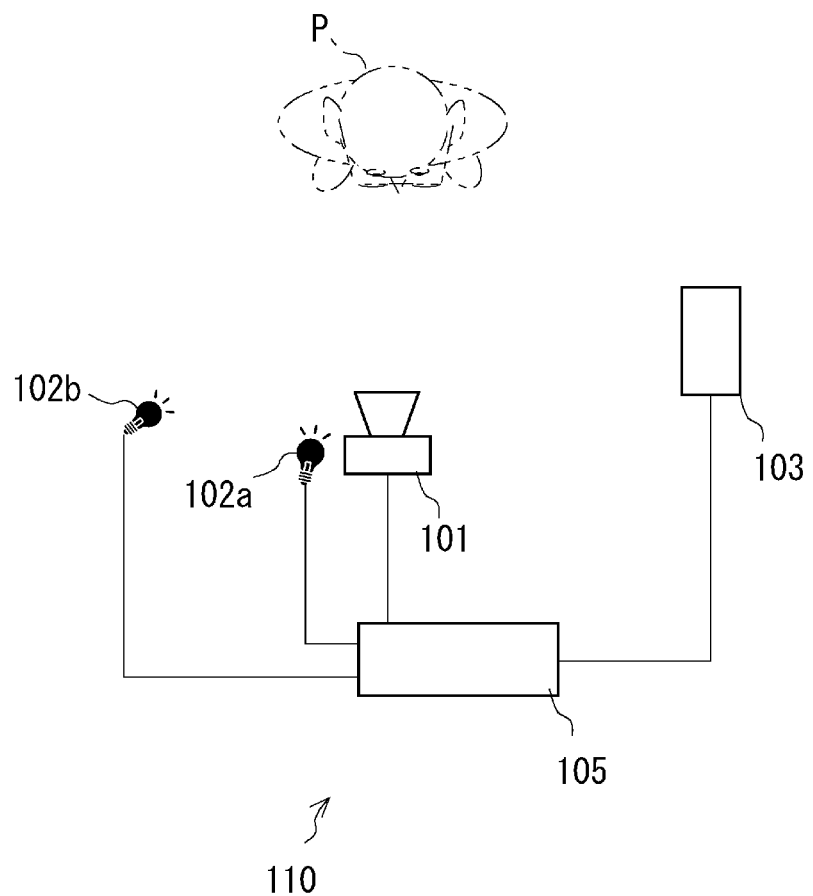
FIG. 4 is a block diagram showing a configuration of an imaging system according to a third example embodiment.

Firstly, an example of a configuration of an imaging system according to the third example embodiment will be described. FIG. 4 is a block diagram showing a configuration of an imaging system 110 according to the third example embodiment. As shown in FIG. 4, the imaging system 110 includes an iris imaging device (iris imaging means) 101, a first illuminator (first illumination means) 102a, a second illuminator (second illumination means) 102b, a guiding device (guiding means) 103, and a controller (controlling means) 105.

The iris imaging device 101 is a camera for photographing an iris(es) of a subject P. The iris imaging device 101 is disposed so as to be able to properly photographing a focusing area including an eye(s) of the subject P who is present (e.g., standing) at a predetermined position. The iris imaging device 101 is composed of, for example, a general-purpose camera having a resolution of 12 M pixels (4,000 pixels in the horizontal direction and 3,000 pixels in the vertical direction) and a frame rate of 60 fps, which is becoming popular as an industrial camera or the like.

Each of the first illuminator 102a and the second illuminator 102b includes an LED(s) (Light Emitting Diode) as a light source and a synchronization signal generator. The amount of light emitted from each of the first and second illuminators 102a and 102b to the subject P is determined by the value (i.e., the amount) of the current supplied to the LED(s), the lighting time (i.e., the lighting duration) of the LED(s), and the lighting cycle thereof, and illumination control information includes these numerical values. Note that the arrangement of the first and second illuminators 102a and 102b will be described later.

The guiding device 103 is used to guide the subject P. The guiding device 103 includes a speaker. The guiding device 103 presents (i.e., outputs) a voice for guiding the subject P from the speaker. From the speaker, for example, a voice guidance for guiding the subject P such as "Take a couple of steps forward", "Step backward", or "Stop" is output.

The controller 105 determines whether or not the subject P is wearing glasses or the like, and controls the operations performed by the first illuminator 102a, the second illuminator 102b, and the guiding device 103 based on the result of the determination. Further, the controller 105 also controls the operation performed by the iris imaging device 101. As a method for determining whether or not the subject P is wearing glasses or the like, a publicly-known method, for example, a method for checking whether or not diffused reflection occurs due to lenses such as glasses or the like disclosed in Patent Literature 1, may be used.

Next, the arrangement of the first and second illuminators 102a and 102b will be described.

Figure 5:
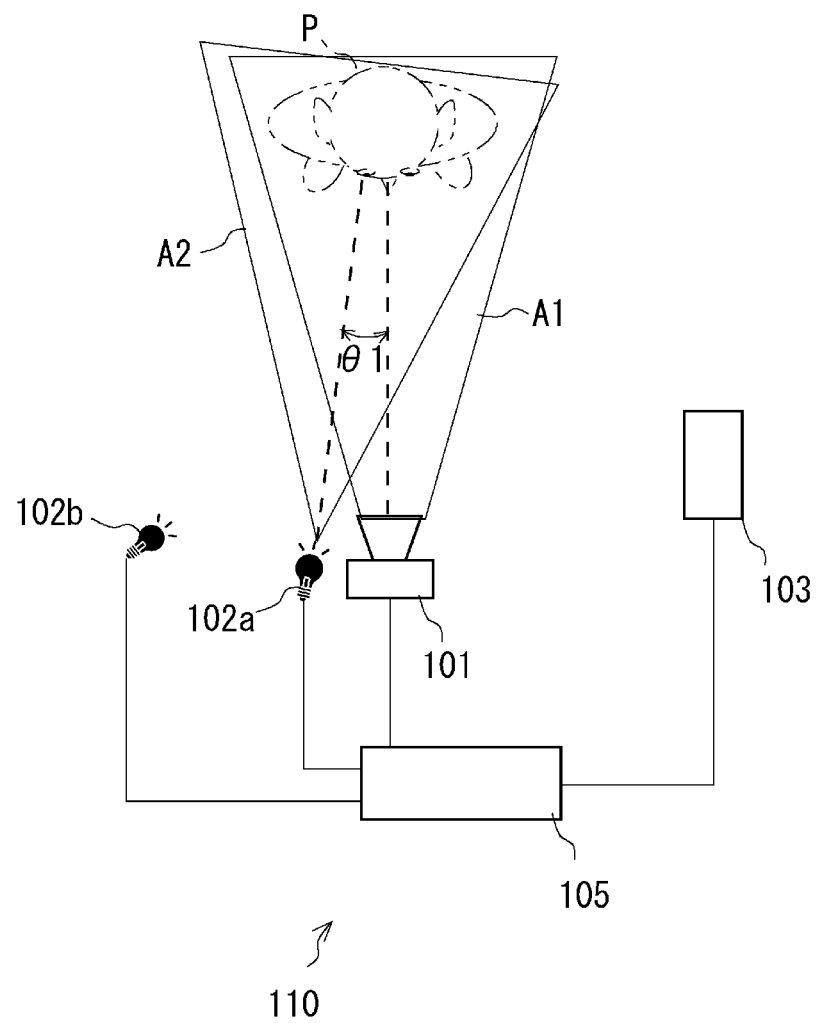
FIG. 5 is a schematic diagram for explaining a position of a first illuminator in the imaging system according to the third example embodiment.

FIG. 5 is a schematic diagram for explaining the position of the first illuminator 102a. The first illuminator 102a applies light to the subject P when the controller 105 has determined that the subject is not wearing glasses or the like (naked eyes). As shown in FIG. 5, an angle between the optical axis of light emitted from the first illuminator 102a and the optical axis of the iris imaging device 101 is represented by an angle θ1. The angle θ1 is determined empirically and experimentally so that the overlapping range between the imaging range A1 of the iris imaging means 1 and the irradiation range A2 of the first irradiation means 2a becomes as large as possible.

Figure 6:
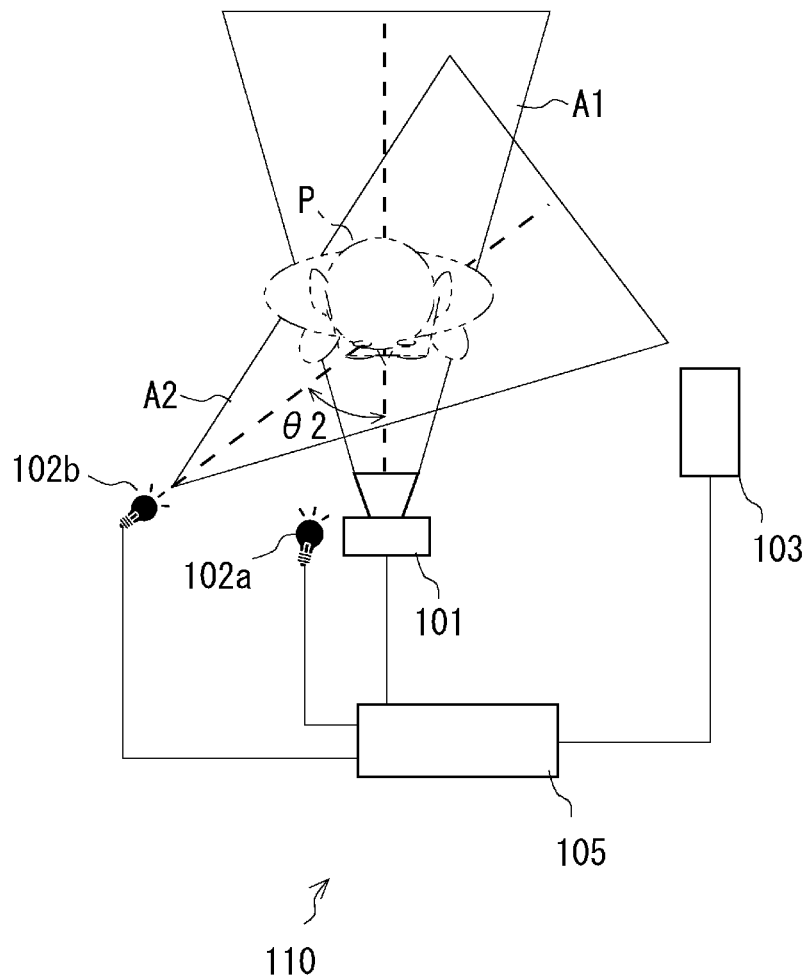
FIG. 6 is a schematic diagram for explaining a position of a second illuminator in the imaging system according to the third example embodiment.

FIG. 6 is a schematic diagram for explaining the position of the second illuminator 102b. The second illuminator 102b applies light to the subject P when the controller 105 has determined that the subject is wearing glasses or the like. As shown in FIG. 6, an angle between the optical axis of light emitted from the second illuminator 102b and the optical axis of the iris imaging device 101 is represented by an angle θ2. The angle θ2 is larger than the angle θ1 (θ2>θ1). The angle θ2 is set so that, assuming the curvature of lenses of ordinary glasses or the like, light reflected on the glasses or the like does not overlap (i.e., does not enter) the iris area.

Next, a flow of an imaging process performed in the imaging system 110 will be described. Note that the following description will be given while also referring to FIG. 4 as appropriate.

Figure 7:
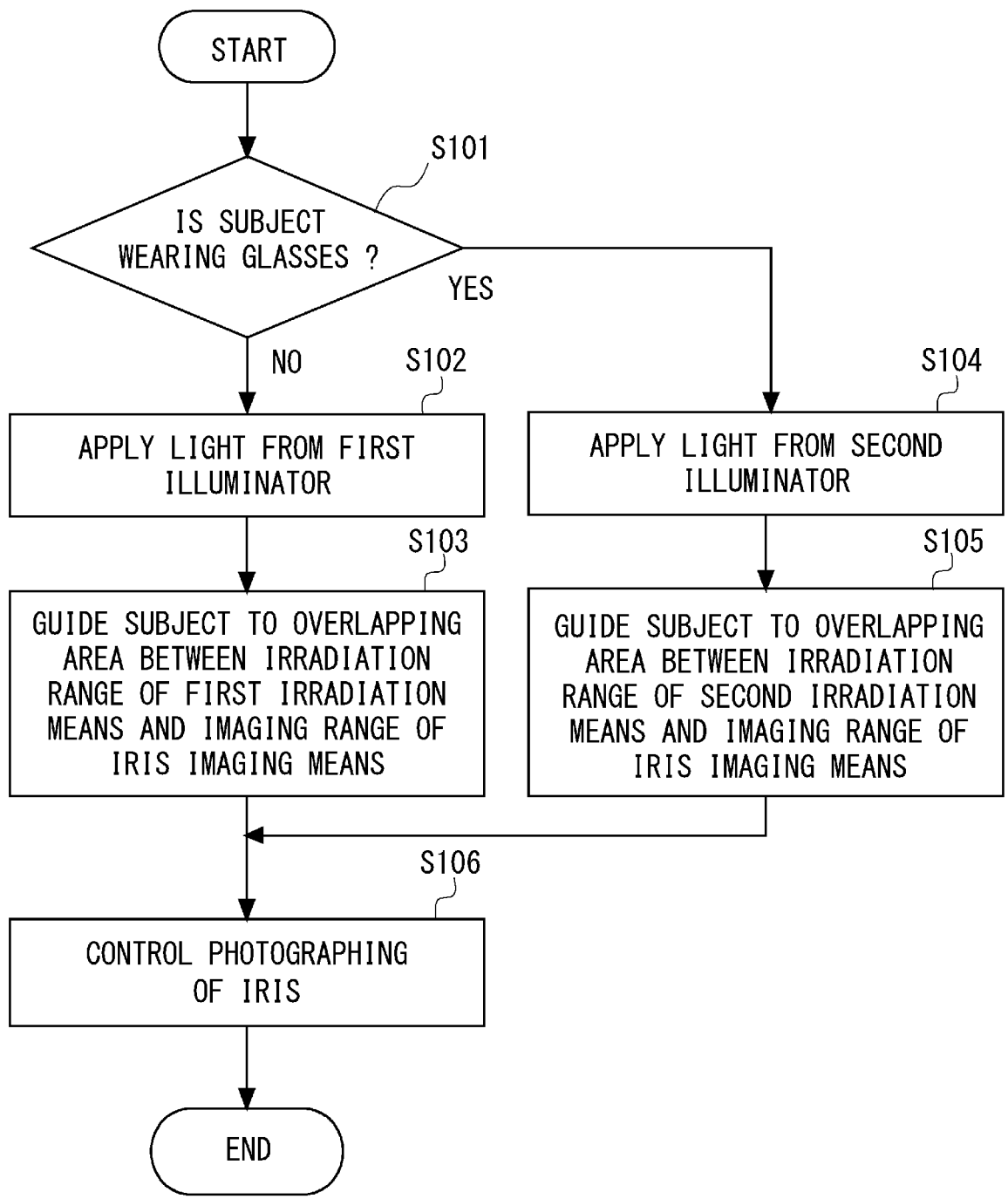
FIG. 7 is a flowchart for explaining a flow of an imaging process in the imaging system according to the third example embodiment.

FIG. 7 is a flowchart for explaining a flow of an imaging process performed in the imaging system 110. As shown in FIG. 7, firstly, the controller 105 determines whether or not the subject is wearing glasses or the like (Step S101).

In the step S101, when the controller 105 determines that the subject is not wearing glasses or the like (No), the controller 105 operates the first illuminator 102a so that light is emitted from the first illuminator 102a (Step S102). Next, the controller 105 operates the guiding device 103 so that the subject is guided so as to move to the overlapping range between the irradiation range of the first illuminator 102a and the imaging range of the iris imaging device 101 (Step S103).

In the step S101, when the controller 105 determines that the subject is wearing glasses or the like (Yes), the controller 105 operates the second illuminator 102b so that light is emitted from the second illuminator 102b (Step S104). Next, the controller 105 operates the guiding device 103 so that the subject is guided so as to move to the overlapping range between the irradiation range of the second illuminator 102b and the imaging range of the iris imaging device 101 (Step S105).

Subsequent to the step S103 or S105, the controller 105 acquires a captured image of an iris(es) by controlling the iris imaging device 101 (Step S106). The captured image of the iris(es) acquired in the step S106 is used for iris authentication or registration.

As described above, in the imaging system 110 according to the third example embodiment, the controller 105 determines whether or not the subject is wearing glasses or the like. Then, when the controller 105 determines that the subject is not wearing glasses or the like, the controller 105 operates the guiding device 103 so that the subject is guided so as to move to the overlapping range between the irradiation range of the first illuminator 102a and the imaging range of the iris imaging device 101, and operates the first illuminator 2a so that light is emitted from the first illuminator 102a.

On the other hand, when the controller 105 determines that the subject is wearing glasses or the like, the controller 105 operates the guiding device 103 so that the subject is guided so as to move to the overlapping range between the irradiation range of the second illuminator 102b and the imaging range of the iris imaging device 101, and operates the second illuminator 102b so that light is emitted from the second illuminator 102b.

By emitting light from the second illuminator 102b when the subject is wearing glasses or the like, it is possible to prevent (or reduce) the reflected light from the glasses or the like from entering the iris imaging means 1. The overlapping range between the irradiation range of the first illuminator 102a and the imaging range of the iris imaging device 101 is larger than the overlapping range between the irradiation range of the second illuminator 102b and the imaging range of the iris imaging device 101. When the subject is not wearing glasses or the like, there is no need to take the prevention (or the reduction) of the reflected light from the glasses or the like into consideration. Therefore, light is emitted from the first illuminator 2a of which the overlapping range with the imaging range of the iris imaging device 1 is large. As a result, when the subject is not wearing glasses or the like, the guiding of the subject becomes easier, so that the convenience is improved.

Fourth Example Embodiment

A fourth example embodiment will be described hereinafter.

Figure 8:
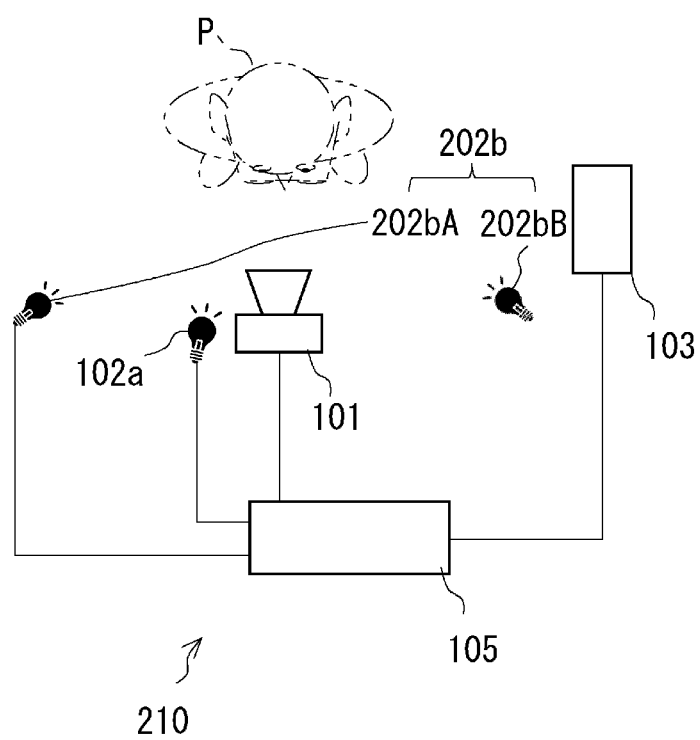
FIG. 8 is a block diagram showing a configuration of an imaging system according to a fourth example embodiment.

FIG. 8 is a block diagram showing a configuration of an imaging system 210 according to a fourth example embodiment. As shown in FIG. 8, the imaging system 210 includes an iris imaging device 101, a first illuminator 102a, a second illuminator 202b, a guiding device 103, and a controller 105. That is, in the imaging system 210, the configuration of the second illuminator 202b is different from that of the imaging system 110 according to the above-described third example embodiment (see FIG. 4). The second illuminator 202b has a left-eye illuminator (left-eye irradiation means) 202bA and a right-eye illuminator (right-eye irradiation means) 202bB.

Figure 9:
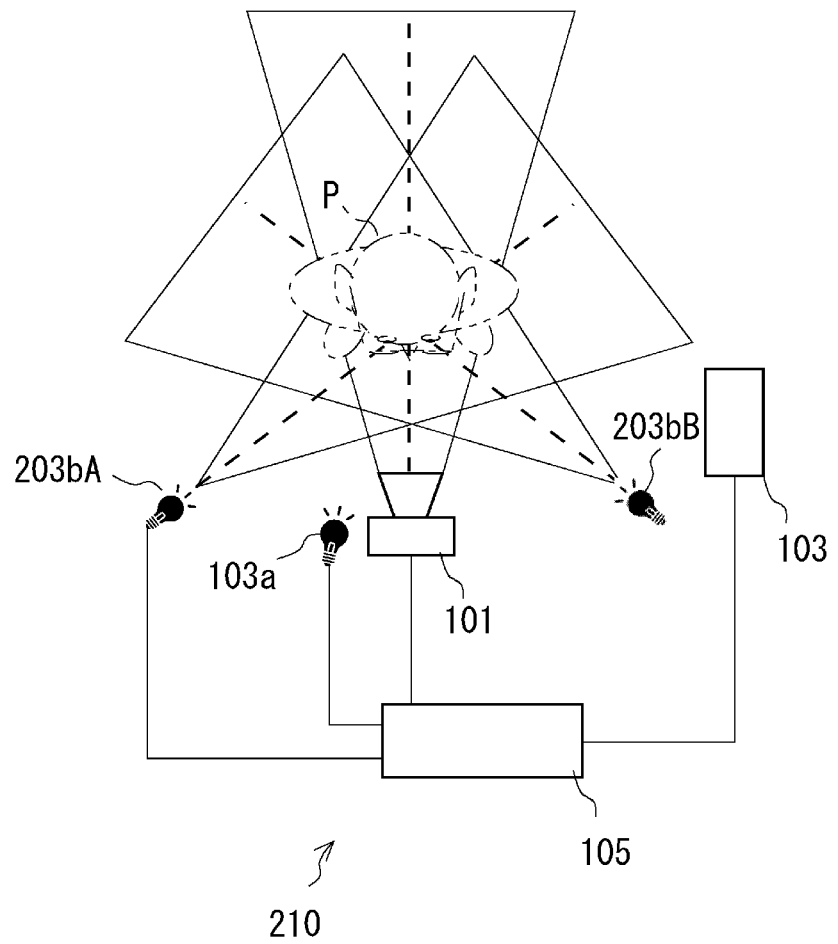
FIG. 9 is a schematic diagram for explaining a position of a second illuminator of the imaging system according to the fourth example embodiment.

FIG. 9 is a schematic diagram for explaining the position of the second illuminator 102b. As shown in FIG. 9, the left-eye illuminator 202bA is disposed at a position appropriate for photographing the iris of the left eye of the subject P. Further, the right-eye illuminator 202bB is disposed at a position appropriate for photographing the iris of the right eye of the subject P.

The flow of the imaging process performed in the imaging system 210 is basically the same as that performed in the imaging system 110 according to the third example embodiment described above with reference to FIG. 3 or 7. In the step S3 in FIG. 3 or the step S104 in FIG. 7, when a captured image of the iris of the left eye of the subject P is acquired, light is applied from the left-eye illuminator 202bA to the subject P. Further, when a captured image of the iris of the left eye of the subject P is acquired, light is applied from the right-eye illuminator 202bB to the subject P. In this way, it is possible to acquire captured images of the irises of both eyes of the subject P with high accuracy.

Note that when it is desired to acquire captured images of the irises of both eyes of the subject P in one imaging operation, light is applied from both the left-eye and right-eye illuminators 202bA and 202bB to the subject P in the step S3 in FIG. 3 or the step S104 in FIG. 7. However, the accuracy of captured images of the irises can be improved by separately acquiring a captured image of the iris of the left eye of the subject P by applying light from the left-eye illuminator 202bA to the subject P and acquiring a captured image of the iris of the right eye of the subject P by applying light from the right-eye illuminator 202bB to the subject P. This is because the effect of preventing (or reducing) reflection is high when a captured image of the iris of only one of the eyes is acquired by turning on only a respective one of the left-eye and right-eye illuminators 202bA and 202bB.

Fifth Example Embodiment

A fifth example embodiment will be described hereinafter.

Figure 10:
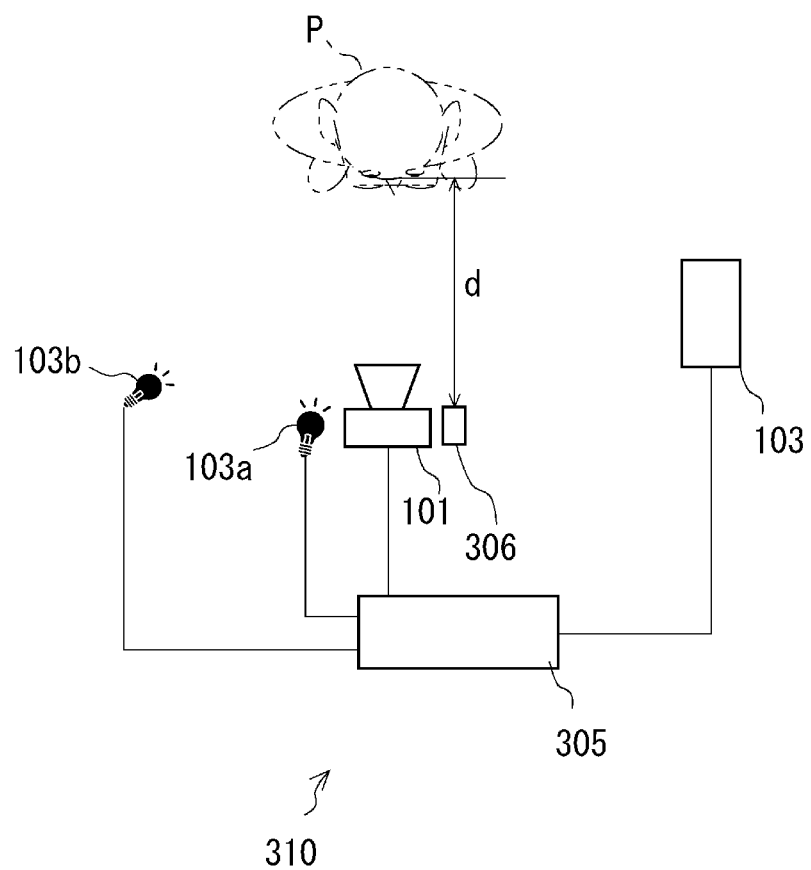
FIG. 10 is a block diagram showing a configuration of an imaging system according to a fifth example embodiment.

FIG. 10 is a block diagram showing a configuration of an imaging system 310 according to the fifth example embodiment. As shown in FIG. 10, the imaging system 310 includes an iris imaging device 101, a first illuminator 102a, a second illuminator 102b, a guiding device 103, a controller 305, and a range sensor 306. That is, the imaging system 210 is different from the imaging system 110 according to third example embodiment described above (see FIG. 4) in that the imaging system 210 further includes a range sensor (distance measuring means) 306. The range sensor 306 measures a distance between the face of the subject P and the iris imaging device 101. Further, the controller 305 includes the functions of the controller 105 of the imaging system 110 according to the third example embodiment.

The flow of the imaging process performed in the imaging system 310 is basically the same as that performed in the imaging system 110 according to the third example embodiment described above with reference to FIG. 7, but the process in the step S105 in FIG. 7 is different in the imaging system 310. In the imaging system 310, in the step S105 in FIG. 7, the controller 305 determines whether or not the subject is present at a distance d from the imaging device based on the result of the distance measurement by the range sensor 306. When the subject is not present at the distance d from the imaging device, the controller 305 operates the guiding device 103 so that the subject P is guided so as to move to the overlapping range between the irradiation range of the second illuminator 102b and the imaging range of the iris imaging device 101. Further, in the step S105 in FIG. 7, the controller 305 operates the guiding device 103 so that the subject P is guided to a position where the distance measured by the range sensor 306 becomes equal to a predetermined length d which is determined according to the angle between the optical axis of light emitted from the second illuminator 102b and the optical axis of the iris imaging means. By determining whether or not the subject is present at the distance d from the imaging device based on the result of the distance measurement, and guiding the subject only when the subject is not present at the distance d from the imaging device as described above, it is possible to skip the unnecessary guiding operation.

When the subject is guided to the above-described position as described above, the controller 305 operates the iris imaging device 101 so that the iris imaging device 101 photographs the iris(es) of the subject in the step S106.

Figure 11:
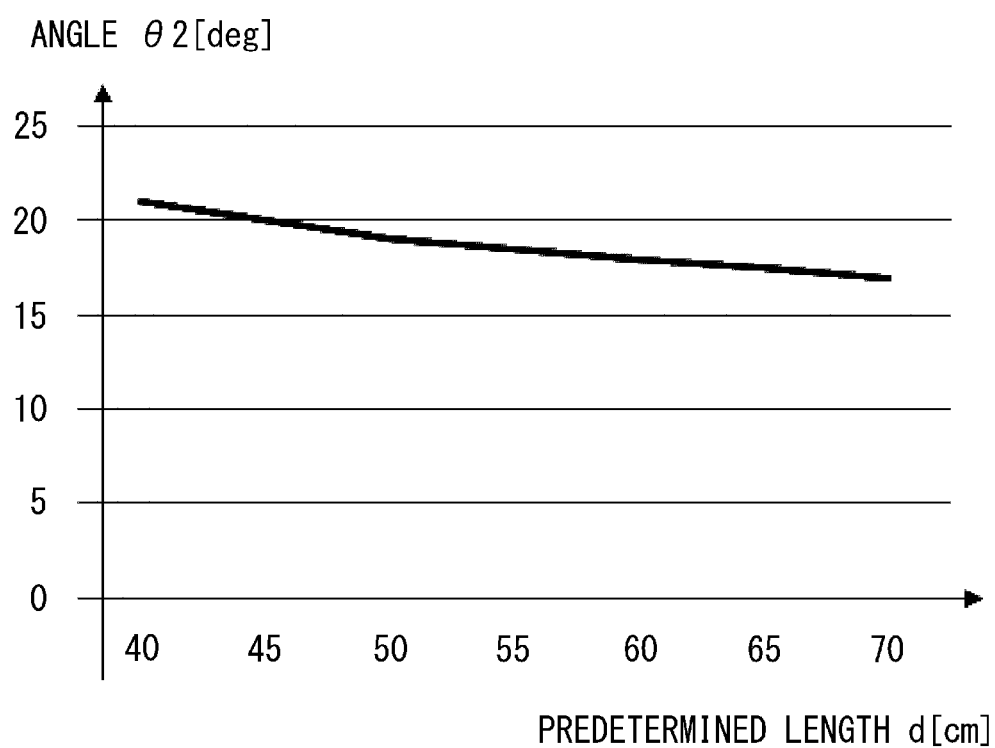
FIG. 11 is a graph showing a relationship between a predetermined length, and an angle between the optical axis of light applied by a second illuminator and the optical axis of an iris imaging device.

FIG. 11 is a graph showing an example of a relationship between the predetermined length d and the angle θ2 between the optical axis of light emitted from the second illuminator 102b and the optical axis of the iris imaging device 101. As shown in FIG. 11, the predetermined length d is determined according to the angle θ2 between the optical axis of light emitted from the second illuminator 102b and the optical axis of the iris imaging device 101. For example, when the angle θ2 between the optical axis of light emitted from the second illuminator 102b and the optical axis of the iris imaging device 101 is 20 [deg], the predetermined length d is 45 [cm].

As described above, the angle θ2 is set so that light reflected on the glasses or the like does not overlap (i.e., does not enter) the iris area. The angle at which light reflected on the glasses or the like does not overlap the iris area can be calculated by assuming (i.e., using) the curvature of lenses of ordinary glasses or the like. When the angle θ2 is determined, the predetermined length can be determined from the graph shown in FIG. 11.

As described above, in the imaging system 310, when it is determined that the subject is wearing glasses or the like, the subject is guided to a position which is located in the overlapping range between the irradiation range of the second illuminator 102b and the imaging range of the iris imaging device 101, and where the distance between the range sensor 306 and the face of the subject is equal to the predetermined length d. In this way, it is possible to improve the accuracy of the acquired captured image even further. Further, it is possible, by performing iris authentication by using the above-described captured image, to improve the success rate of the iris authentication.

Sixth Example Embodiment

A sixth example embodiment will be described hereinafter.

Figure 12:
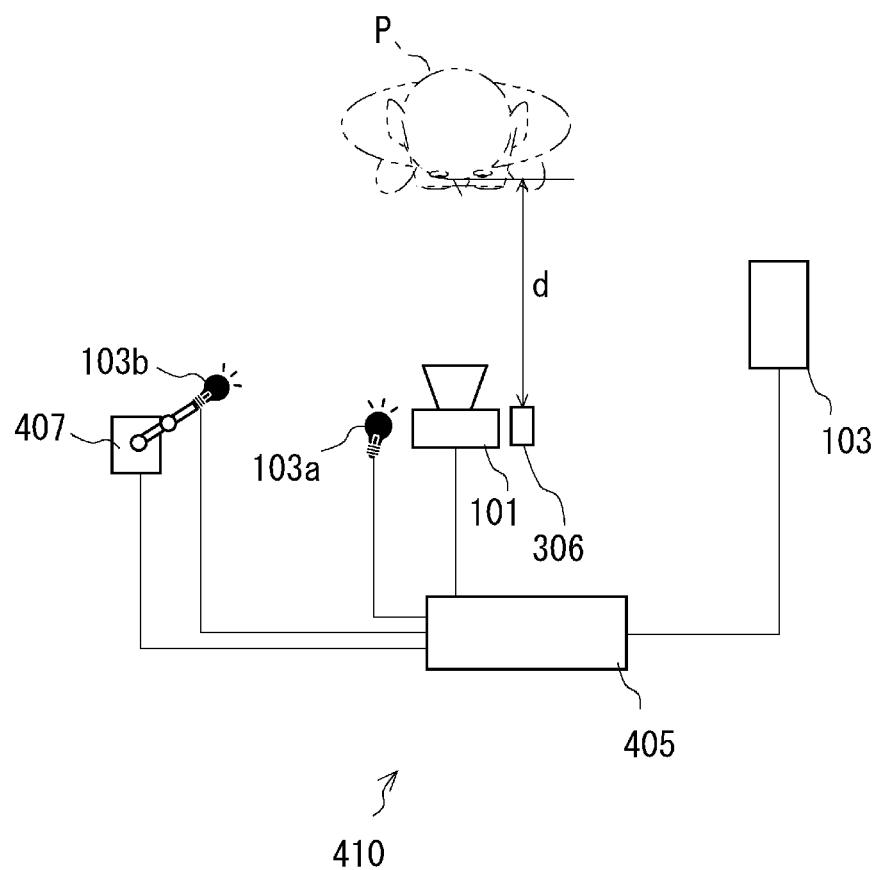
FIG. 12 is a block diagram showing a configuration of an imaging system according to a sixth example embodiment.

FIG. 12 is a block diagram showing a configuration of an imaging system 410 according to the sixth example embodiment. As shown in FIG. 12, the imaging system 410 includes an iris imaging device 101, a first illuminator 102a, a second illuminator 102b, a guiding device 103, a controller 305, a range sensor 306, and a position adjustment device 407. That is, the imaging system 410 is different from the imaging system 310 according to the fifth example embodiment described above (see FIG. 10) in that the imaging system 410 further includes a position adjustment device (position adjustment means) 407. The position adjustment device 407 is used to adjust the position of the second illuminator 102b.

Figure 13:
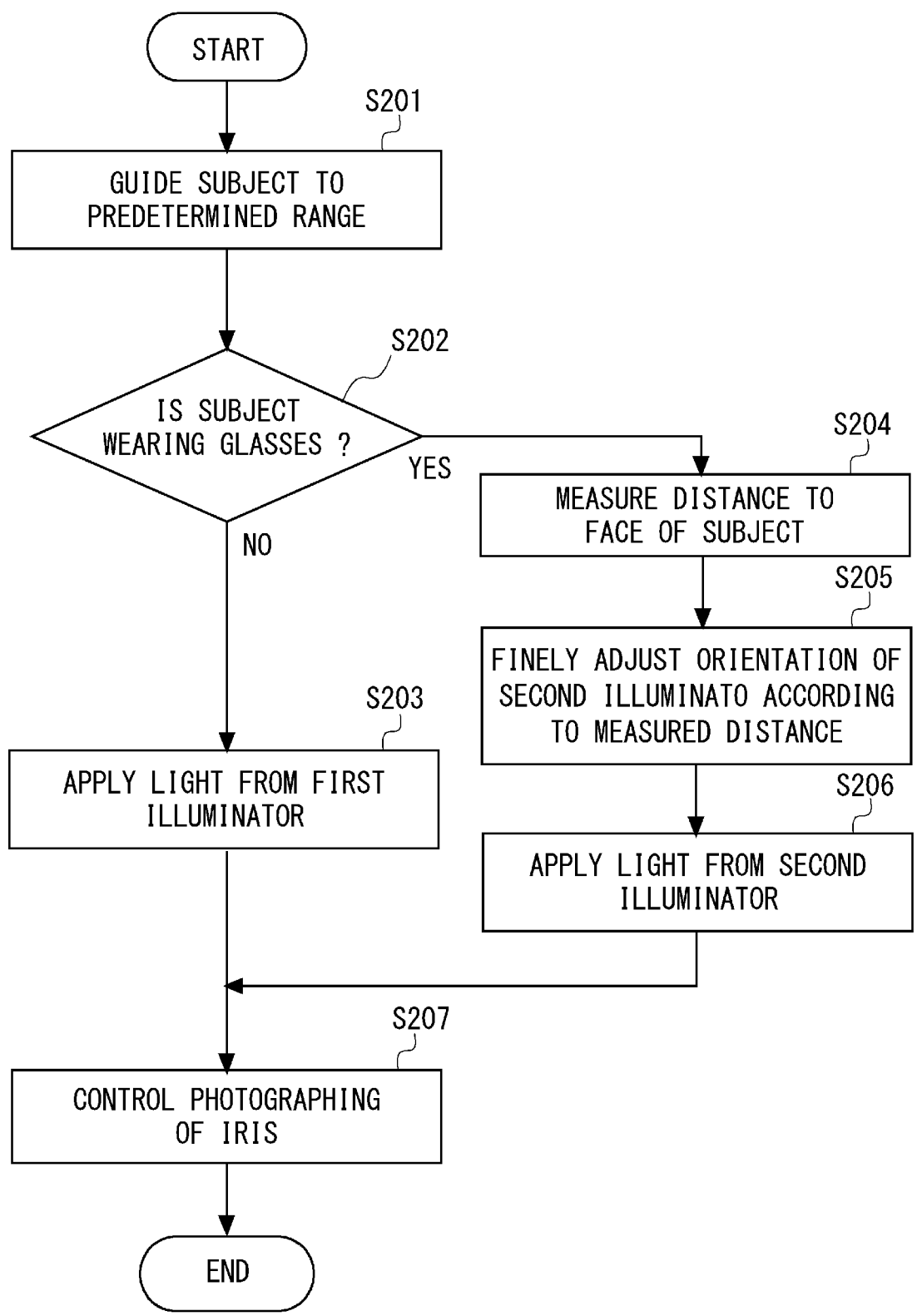
FIG. 13 is a flowchart for explaining a flow of an imaging process in the imaging system according to sixth example embodiment.

FIG. 13 is a flowchart for explaining a flow of an imaging process performed in the imaging system 410. As shown in FIG. 13, firstly, a subject is guided so as to move to a predetermined range (Step S201). Note that the predetermined range is, for example, the overlapping range between the irradiation range of the first illuminator 102a and the imaging range of the iris imaging device 101. Next, the controller 405 determines whether or not the subject is wearing glasses or the like (Step S202).

In the step S202, when the controller 405 determines that the subject is not wearing glasses or the like (No), the controller 405 operates the first illuminator 102a so that light is emitted from the first illuminator 102a (Step S203).

In the step S202, when the controller 405 determines that the subject is wearing glasses or the like (Yes), a distance to the face of the subject is measured by the range sensor 306 (Step S204). Next, the controller 405 operates the position adjustment device 407 so that the angle between the optical axis of light emitted from the second illuminator 102b and the optical axis of the iris imaging means becomes equal to a predetermined angle that is determined according to the distance measured by the range sensor 306 (Step S205). Next, the controller 405 operates the second illuminator 102b so that light is emitted from the second illuminator 102b (Step S206).

Subsequent to the step S203 or S206, the controller 405 acquires a captured image of an iris(es) by controlling the iris imaging device 101 to (Step S207). The captured image of the iris(es) acquired in the step S207 is used for iris authentication or registration.

Seventh Example Embodiment

A seventh example embodiment will be described hereinafter.

Figure 14:
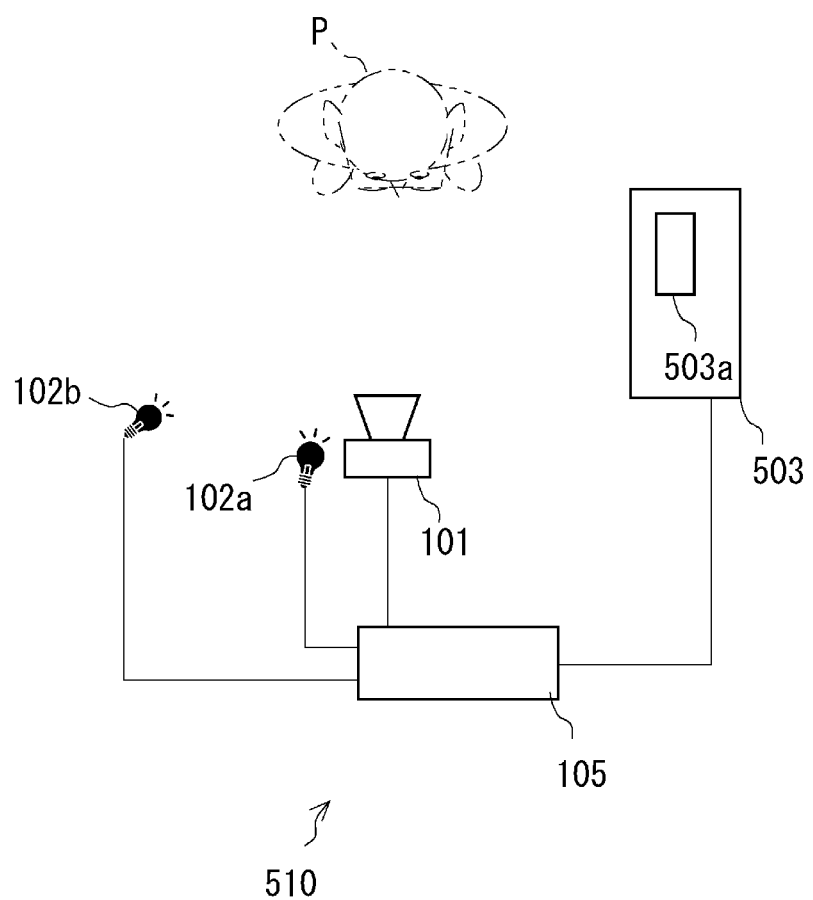
FIG. 14 is a block diagram showing a configuration of an imaging system according to a seventh example embodiment.

FIG. 14 is a block diagram showing a configuration of an imaging system 510 according to the seventh example embodiment. As shown in FIG. 14, the configuration of the imaging system 510 according to the seventh example embodiment is basically the same as that of the imaging system 110 according to the third example embodiment described above with reference to FIG. 4. In the imaging system 510 according to the seventh example embodiment, the configuration of a guiding device 503 is different from the configuration of the guiding device 103 of the imaging system 110 according to the third example embodiment. The guiding device 503 includes a display 503a. The guiding device 503 presents (i.e., shows) a video image for guiding the subject P on the display 503a.

Figure 15:
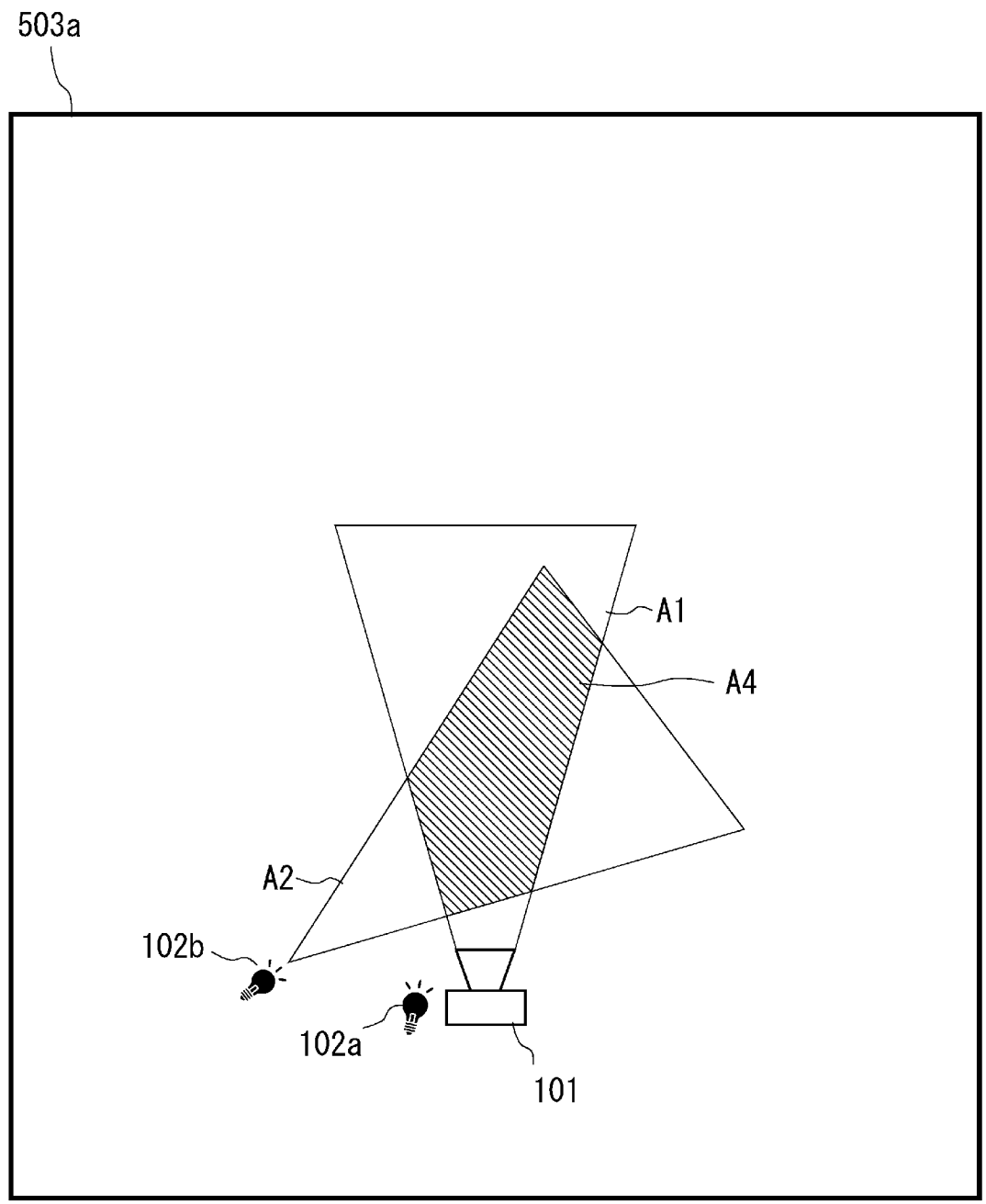
FIG. 15 is a schematic diagram showing an example of an image displayed on a display of a guiding device in the imaging system according to the seventh example embodiment.

FIG. 15 is a schematic diagram showing an example of the image displayed on the display 503a. As shown in FIG. 15, the irradiation range of the illuminator (the irradiation range A2 of the second illuminator 102b in FIG. 15) and the imaging range A1 of the iris imaging device 101 are displayed on the display 503a. Note that when light is emitted from the first illuminator 102a, the irradiation range of the first illuminator 102a is displayed as the irradiation range of the illuminator on the display 503a. On the display 503a, as the video image for guiding the subject P, an overlapping range A4 between the irradiation range of the illuminator and the imaging range of the iris imaging device 101 is highlighted by hatching. Note that, instead of highlighting the overlapping range A4 by hatching, the overlapping range A4 may be highlighted by a different method such as simply adding a circular mark inside the overlapping range A4. It is possible to properly guide the subject by configuring the guiding device 503 as described above.

Eighth Example Embodiment

An eighth example embodiment will be described hereinafter.

Figure 16:
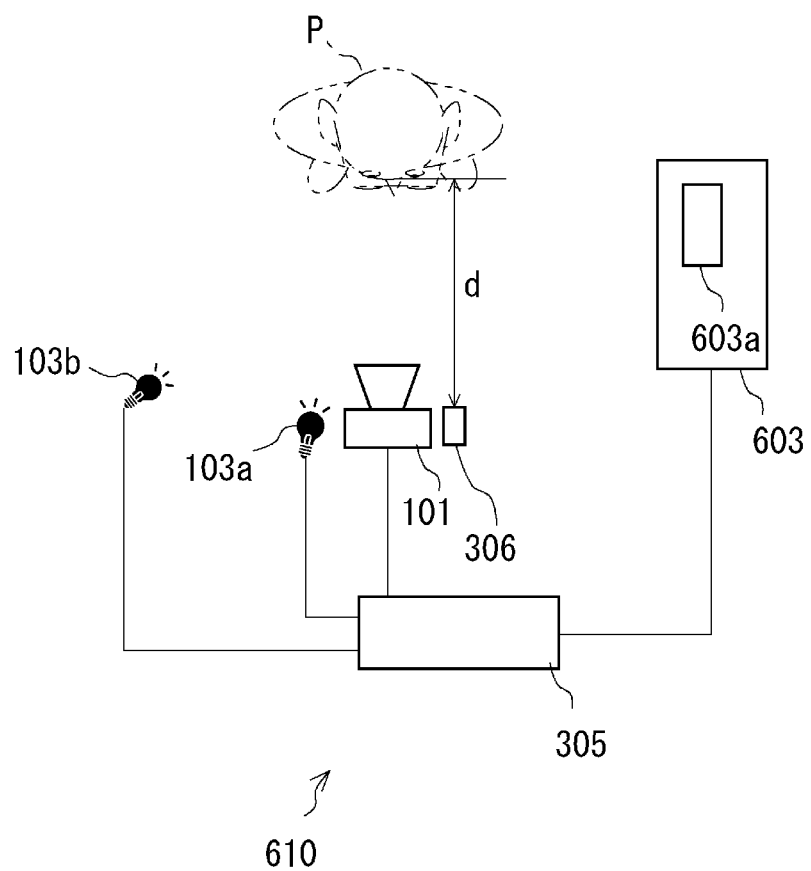
FIG. 16 is a block diagram showing a configuration of an imaging system according to an eighth example embodiment.

FIG. 16 is a block diagram showing a configuration of an imaging system 610 according to the eighth example embodiment. As shown in FIG. 16, the configuration of the imaging system 610 according to the eighth example embodiment is basically the same as that of the imaging system 310 according to the fifth example embodiment described above with reference to FIG. 10. In the imaging system 610 according to the eighth example embodiment, a guiding device 603 is different from the guiding device 103 of the imaging system 310 according to the fifth example embodiment. The guiding device 603 includes a display 603a. The guiding device 603 presents (i.e., shows) a video image for guiding the subject P on the display 603a.

Figure 17:
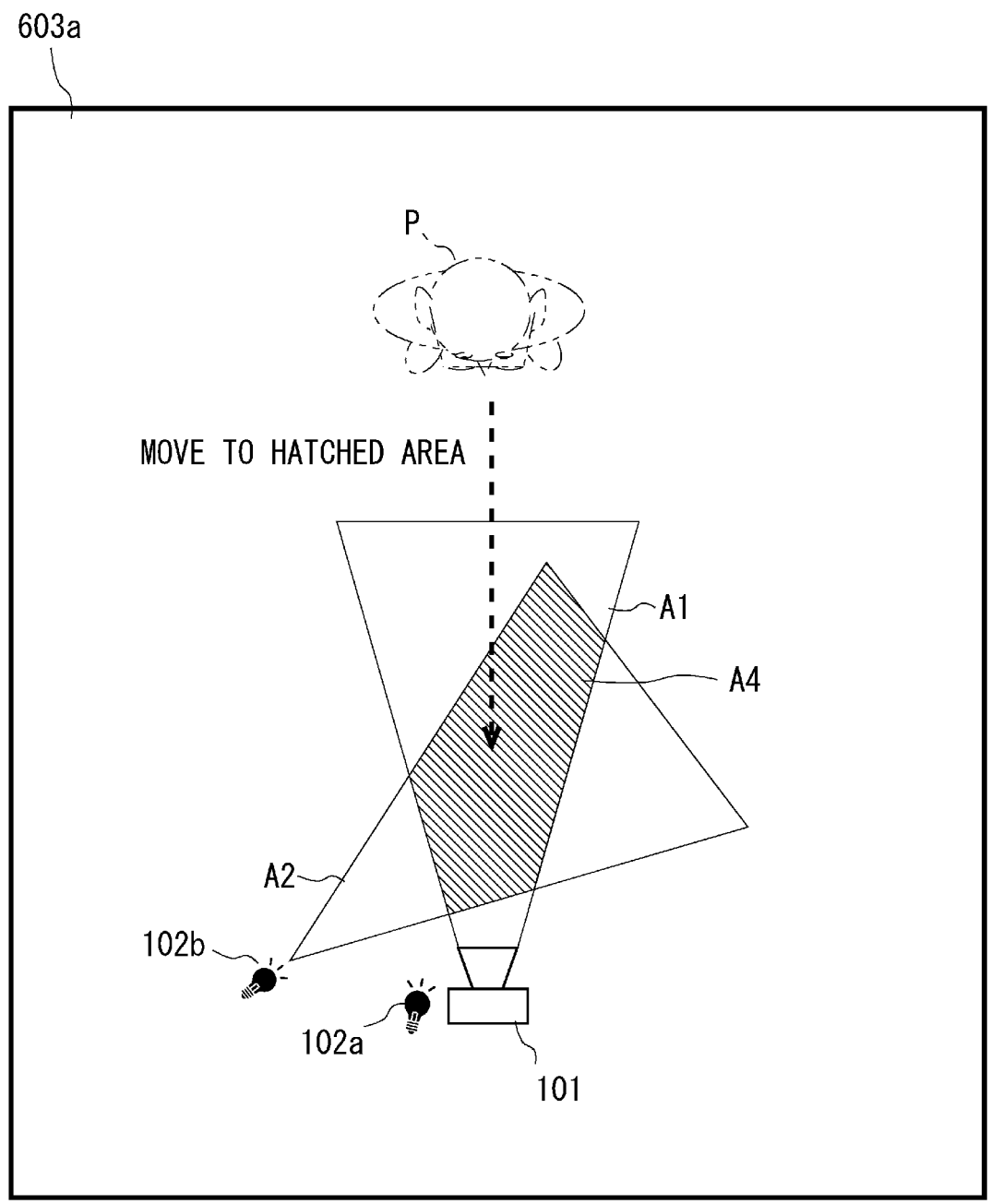
FIG. 17 is a schematic diagram showing an example of an image displayed on a display of a guiding device in the imaging system according to the eighth example embodiment.

FIG. 17 is a schematic diagram showing an example of the image displayed on the display 603a. As shown in FIG. 15, the irradiation range of the illuminator (the irradiation range A2 of the second illuminator 102b in FIG. 15) and the imaging range A1 of the iris imaging device 101 are displayed on the display 603a. Note that when light is emitted from the first illuminator 102a, the irradiation range of the first illuminator 102a is displayed as the irradiation range of the illuminator on the display 603a. Further, the position of the subject P is displayed on the display 603a. Note that the position of the subject P is specified by the range sensor 306. Further, on the display 603a, as the video image for guiding the subject P, an overlapping range A4 between the irradiation range of the illuminator and the imaging range of the iris imaging device 101 is highlighted by hatching, and the direction in which the subject P should move is indicated by an arrow. Further, an instruction "Move to the hatched range" is displayed. It is possible to guide the subject P in a more appropriate manner by configuring the guiding device 603 as described above.

Ninth Example Embodiment

A ninth example embodiment will be described hereinafter.

Figure 18:
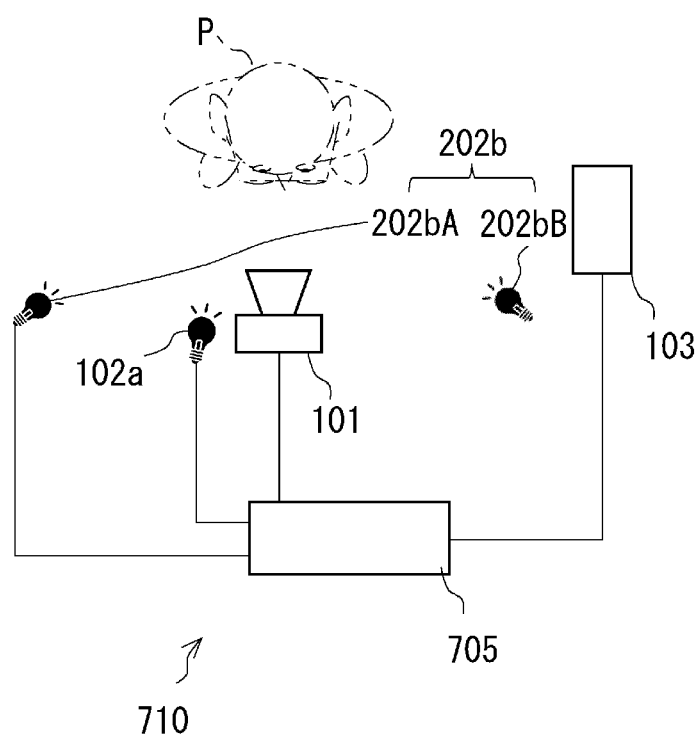
FIG. 18 is a block diagram showing a configuration of an imaging system according to a ninth example embodiment.

FIG. 18 is a block diagram showing a configuration of an imaging system 710 according to the ninth example embodiment. As shown in FIG. 18, the imaging system 710 includes an iris imaging device 101, a first illuminator 102a, a second illuminator 202b, a guiding device 103, and a controller 705. In the imaging system 710, the process performed in the controller 705 is different from that performed in the controller 105 of the imaging system 210 according to the fourth example embodiment.

Figure 19:
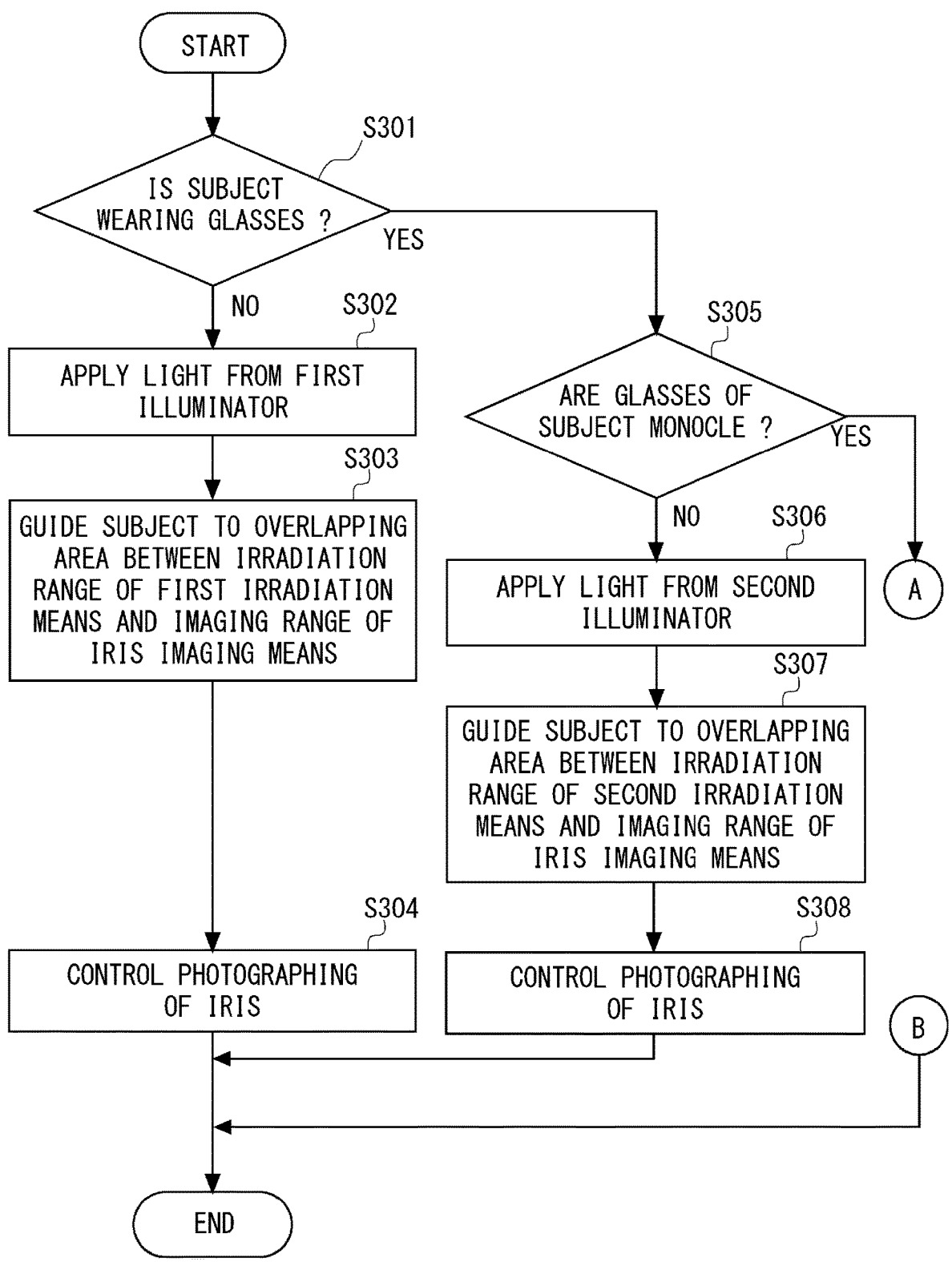
FIG. 19 is a flowchart for explaining a flow of an imaging process in the imaging system according to the ninth example embodiment.
Figure 20:
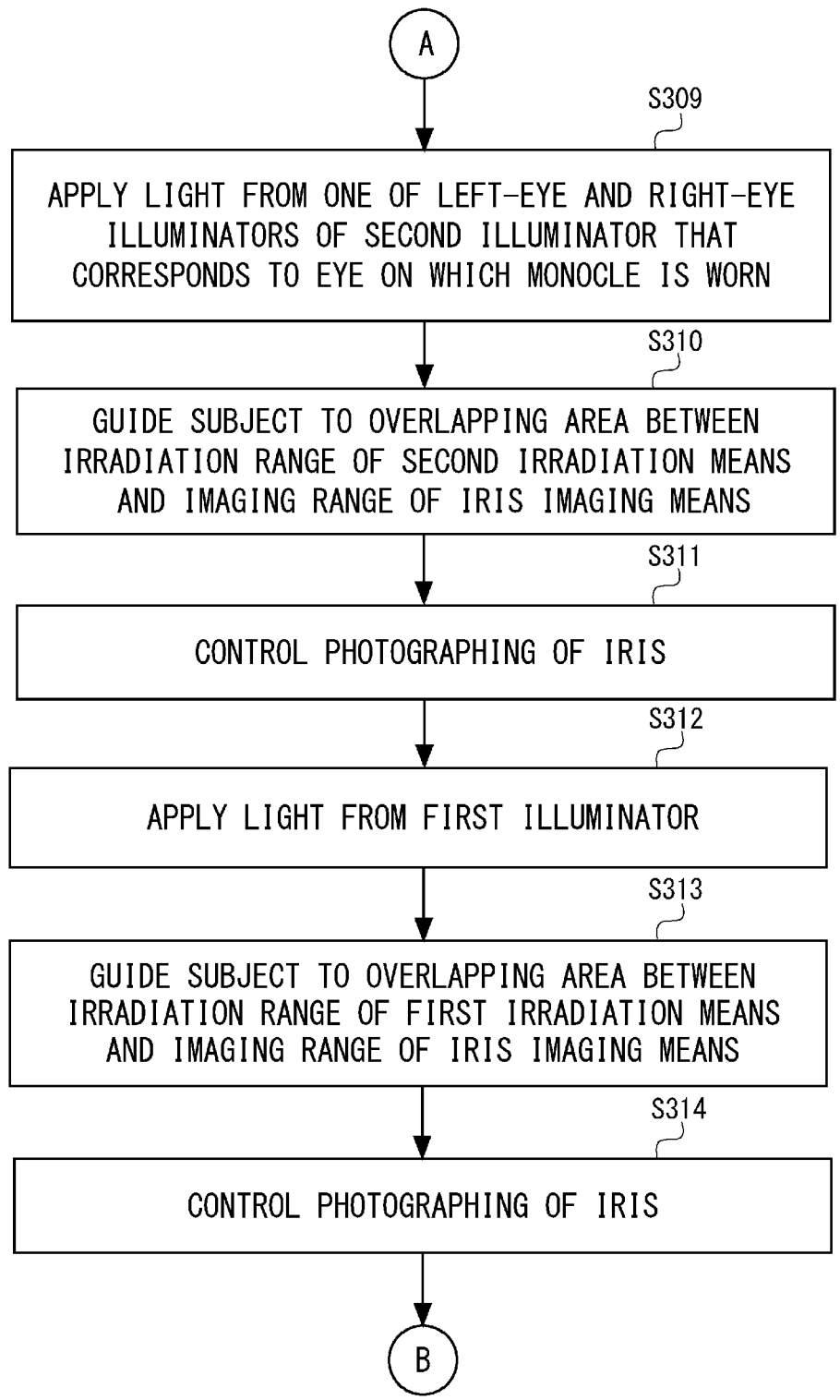
FIG. 20 is a flowchart for explaining a flow of an imaging process in the imaging system according to the ninth example embodiment.

FIGS. 19 and 20 are flowcharts for explaining a flow of an imaging process performed in the imaging system 710 according to the ninth example embodiment. As shown in FIG. 19, firstly, the controller 705 determines whether or not the subject is wearing glasses or the like (Step S301).

In the step S301, when the controller 705 determines that the subject is not wearing glasses or the like (No), the controller 705 operates the first illuminator 102a so that light is emitted from the first illuminator 102a (Step S302). Next, the controller 705 operates the guiding device 103 so that the subject is guided so as to move to the overlapping range between the irradiation range of the first illuminator 102a and the imaging range of the iris imaging device 101 (Step S303). Next, the controller 705 acquires a captured image of an iris(es) by controlling the iris imaging device 101 (Step S304).

In the step S301, when the controller 705 determines that the subject is wearing glasses or the like (Yes), it determines whether or not the glasses or the like worn by the subject are a monocle (Step S305).

In the step S305, when it is determined that the glasses or the like worn by the subject are not a monocle (No), the controller 705 operates the second illuminator 202b (the left-eye and right-eye illuminators 202bA and 202bB) so that light is emitted from the second illuminator 202b (Step S306). Next, the controller 705 operates the guiding device 103 so that the subject is guided so as to move to the overlapping range between the irradiation range of the second illuminator 202b and the imaging range of the iris imaging device 101 (Step S307). Next, the controller 705 acquires a captured image of an iris(es) by controlling the iris imaging device 101 to (Step S308).

In the step S305, when it is determined that the glasses or the like worn by the subject are a monocle (Yes), the controller 705 operates the second illuminator 202b so that light is emitted from one of the left-eye and right-eye illuminators 202bA and 202bB of the second illuminator 202b that corresponds to the eye on which the monocle is worn as shown in FIG. 20 (Step S309). Next, the controller 705 operates the guiding device 103 so that the subject is guided so as to move to the overlapping range between the irradiation range of the second illuminator 202b and the imaging range of the iris imaging device 101 (Step S310). Note that the irradiation range of the left-eye illuminator 202bA becomes the irradiation range of the second illuminator 202b when light is emitted from the left-eye illuminator 202bA, and the irradiation range of the right-eye illuminator 202bB becomes the irradiation range of the second illuminator 202b when light is emitted from the right-eye illuminator 202bB. Next, the controller 705 acquires a captured image of an iris(es) by controlling the iris imaging device 101 to (Step S311). Next, the controller 705 operates the first illuminator 102a so that light is emitted from the first illuminator 102a (Step S312). In this process, the second illuminator 202b remains in the turned-off state. Next, the controller 705 operates the guiding device 103 so that the subject is guided so as to move to the overlapping range between the irradiation range of the first illuminator 102a and the imaging range of the iris imaging device 101 (Step S313). Next, the controller 705 acquires a captured image of an iris(es) by controlling the iris imaging device 101 to (Step S314).

The captured images of the iris(es) acquired in the steps S304 and S308 in FIG. 19, and those acquired in the steps S311 and S314 in FIG. 20 are used for iris authentication or registration. In this way, in the case where iris authentication is performed for each of the left and right eyes of the subject, it is possible to acquire a captured image of the iris of each of the left and right eyes of the subject, who is wearing the monocle, with high accuracy.

Although the above-described example embodiments have been described on the assumption that this disclosure is implemented as a hardware configuration, this disclosure is not limited to the hardware configuration. In this disclosure, the imaging process performed in any of the imaging systems shown in FIGS. 3, 7, 13 and 18 can also be carried out by having a CPU (Central Processing Unit) execute a program. Further, each process in the imaging operation performed in any of the imaging systems shown in FIGS. 3, 7, 13 and 18 may be carried out by a GPU (Graphics Processing Unit), an FPGA (field-programmable gate array), a DSP (Demand-Side Platform), or an ASIC (Application Specific Integrated Circuit).

The program for implementing the above-described imaging method can be stored in various types of non-transitory computer readable media and thereby supplied to computers. The non-transitory computer readable media includes various types of tangible storage media. Examples of the non-transitory computer readable media include a magnetic recording medium (such as a flexible disk, a magnetic tape, and a hard disk drive), a magneto-optic recording medium (such as a magneto-optic disk), a Compact Disc Read Only Memory (CD-ROM), a CD-R, and a CD-R/W, and a semiconductor memory (such as a mask ROM, a Programmable ROM (PROM), an Erasable PROM (EPROM), a flash ROM, and a Random Access Memory (RAM)). Further, the program can be supplied to computers by using various types of transitory computer readable media. Examples of the transitory computer readable media include an electrical signal, an optical signal, and an electromagnetic wave. The transitory computer readable media can be used to supply programs to computer through a wire communication path such as an electrical wire and an optical fiber, or wireless communication path.

Although the present invention is described above with reference to example embodiments, the present invention is not limited to the above-described example embodiments. Various modifications that can be understood by those skilled in the art can be made to the configuration and details of the present invention within the scope of the invention. For example, although the first and second irradiation means are two-dimensionally arranged, i.e., are arranged so that they are disposed on the same horizontal plane in the above-described example embodiments, their arrangement is not limited to the two-dimensional arrangement. The first and second irradiation means may be three-dimensionally arranged.

In the above-described sixth example embodiment, the angle between the optical axis of light emitted from the second illuminator and the optical axis of the iris imaging means is adjusted by using the position adjustment device. Instead of using such a method, a plurality of second illuminators of which angles between the optical axes of the emitted light and the optical axis of the iris imaging means differ from each other may be provided. In such a case, one of the plurality of second illuminators of which the angle between the optical axis of the emitted light and the optical axis of the iris imaging means is closest to a predetermined angle that is determined according to a distance measured by a range sensor applies light to the subject.

The whole or part of the example embodiments disclosed above can be described as, but not limited to, the following supplementary notes.

(Supplementary note 1)
An imaging system comprising:
  iris imaging means for photographing an iris of a subject;
  first irradiation means for applying light to the subject; and
  second irradiation means for applying light to the subject in such a manner that an angle between an optical axis of the light emitted from the second irradiation means and an optical axis of the iris imaging means is larger than an angle between an optical axis of the light emitted from the first irradiation means and the optical axis of the iris imaging means.

(Supplementary note 2)
The imaging system described in Supplementary note 1, further comprising control means for determining whether or not the subject is wearing glasses or the like, and controlling an operation performed by the first and second irradiation means based on a result of the determination, wherein
  the control means operates the first irradiation means so that light is emitted from the first irradiation means when it is determined that the subject is not wearing glasses or the like, and
  the control means operates the second irradiation means so that light is emitted from the second irradiation means when it is determined that the subject is wearing glasses or the like.

(Supplementary note 3)
The imaging system described in Supplementary note 2, further comprising guiding means for guiding the subject, wherein
  the control means operates the guiding means so that the subject is guided so as to move to an overlapping range between an irradiation range of the first irradiation means and an imaging range of the iris imaging means when it is determined that the subject is not wearing glasses or the like, and
  the control means operates the guiding means so that the subject is guided so as to move to an overlapping range between an irradiation range of the second irradiation means and the imaging range of the iris imaging means when it is determined that the subject is wearing glasses or the like.

(Supplementary note 4)
The imaging system described in Supplementary note 1, wherein the second irradiation means comprises left-eye irradiation means disposed at a position appropriate for photographing an iris of a left eye of the subject and right-eye irradiation means disposed at a position appropriate for photographing an iris of a right eye of the subject.

(Supplementary note 5)
The imaging system described in Supplementary note 3, further comprising distance measurement means for measuring a distance between a face of the subject and the iris imaging means, wherein
  the control means operates the guiding means, when it is determined that the subject is wearing glasses or the like, so that the subject is guided to a position where the distance measured by the distance measurement means becomes equal to a predetermined length determined according to an angle between the optical axis of the light emitted from the second irradiation means and the optical axis of the iris imaging means.

(Supplementary note 6)
The imaging system described in Supplementary note 2, further comprising:
  distance measurement means for measuring a distance between a face of the subject and the iris imaging means; and
  position adjustment means for adjusting a position of the second irradiation means, wherein
  the control means operates the position adjustment means so that an angle between the optical axis of the light emitted from the second irradiation means and the optical axis of the iris imaging means becomes equal to a predetermined angle determined according to the distance measured by the distance measurement means.

(Supplementary note 7)
An imaging method comprising:
  a step of determining whether or not a subject is wearing a glass or the like;
  a step of, when it is determined that the subject is not wearing the glass or the like, applying light to the subject from first irradiation means; and
  a step of, when it is determined that the subject is wearing the glass or the like, applying light to the subject from second irradiation means, the second irradiation means being configured so that an angle between an optical axis of the light emitted from the second irradiation means and an optical axis of iris imaging means is larger than an angle between an optical axis of the light emitted from the first irradiation means and the optical axis of the iris imaging means, the iris imaging means being means for photographing an iris of the subject.

(Supplementary note 8)
A non-transitory computer readable medium storing a program for causing a computer to perform:
  a step of determining whether or not a subject is wearing a glass or the like;
  a step of, when it is determined that the subject is not wearing the glass or the like, applying light to the subject from first irradiation means; and
  a step of, when it is determined that the subject is wearing the glass or the like, applying light to the subject from second irradiation means, the second irradiation means being configured so that an angle between an optical axis of the light emitted from the second irradiation means and an optical axis of iris imaging means is larger than an angle between an optical axis of the light emitted from the first irradiation means and the optical axis of the iris imaging means, the iris imaging means being means for photographing an iris of the subject.

REFERENCE SIGNS LIST

1, 101 IRIS IMAGING DEVICE
2a, 102a FIRST ILLUMINATOR 2b, 102b, 202b SECOND ILLUMINATOR
5, 105, 305, 705 CONTROLLER
10, 110, 210, 310, 410, 510, 610, 710 IMAGING SYSTEM
103, 503, 603 GUIDING DEVICE
202bA LEFT EYE ILLUMINATOR
202bB RIGHT EYE ILLUMINATOR
503a 603a DISPLAY

The invention claimed is:

1. An imaging system comprising:
at least one memory configured to store instructions, and
at least one processor configured to execute the instructions to:
photograph an iris of a subject;
apply first light to the subject;
apply second light to the subject in such a manner that an angle between an optical axis of the second light and an optical axis of photographing the iris is larger than an angle between an optical axis of the first light and the optical axis of photographing the iris;
determine whether or not the subject is wearing glasses or the like;
control the first and second light based on a result of the determination;
guide the subject so that the subject is guided so as to move to an overlapping range between an irradiation range of the first light and an imaging range of photographing the iris when it is determined that the subject is not wearing glasses or the like; and
guide the subject so that the subject is guided so as to move to an overlapping range between an irradiation range of the second light and the imaging range of photographing the iris when it is determined that the subject is wearing glasses or the like,
wherein a display guides the subject, and
wherein an overlapping range between the irradiation range of the first light or the second light and the imaging range of photographing the iris is highlighted on the display.

2. The imaging system according to claim 1,
wherein a direction in which the subject should move is indicated by an arrow on the display, and
wherein an instruction is displayed on the display.

3. The imaging system according to claim 1, further comprising:
the processor configured to execute the instructions to:
determine whether or not the glasses are a monocle when it is determined that the subject is wearing the glasses or the like,
control the second light so that second light corresponding to an eye on which the monocle worn when it is determined that the glasses and like worn by the subject are the monocle.

4. An imaging method comprising:
a step of determining whether or not a subject is wearing a glass or the like;
a step of, when it is determined that the subject is not wearing the glass or the like, applying light to the subject from first irradiation means;
a step of, when it is determined that the subject is wearing the glass or the like, applying light to the subject from second irradiation means, the second irradiation means being configured so that an angle between an optical axis of the light emitted from the second irradiation means and an optical axis of iris imaging means is larger than an angle between an optical axis of the light emitted from the first irradiation means and the optical axis of the iris imaging means, the iris imaging means being means for photographing an iris of the subject;
a step of operating a guiding means so that the subject is guided so as to move to an overlapping range between an irradiation range of the first irradiation means and an imaging range of the iris imaging means when it is determined that the subject is not wearing glasses or the like; and
a step of operates the guiding means so that the subject is guided so as to move to an overlapping range between an irradiation range of the second irradiation means and the imaging range of the iris imaging means when it is determined that the subject is wearing glasses or the like,
wherein the guiding means is a display, and
wherein an overlapping range between the irradiation range of the first irradiation means or the second irradiation means and the imaging range of the iris imaging means is highlighted on the display.

5. The imaging method according to claim 4,
wherein a direction in which the subject should move is indicated by an arrow on the display, and
wherein an instruction is displayed on the display.

6. The imaging method according to claim 4, further comprising:
a step of determining whether or not the glasses are a monocle when it is determined that the subject is wearing the glasses or the like; and
a step of controlling the second irradiation means so that light is emitted from the second irradiation means corresponding to an eye on which the monocle worn when it is determined that the glasses and like worn by the subject are the monocle.

7. A non-transitory computer readable medium storing a program for causing a computer to perform:
a step of determining whether or not a subject is wearing a glass or the like;
a step of, when it is determined that the subject is not wearing the glass or the like, applying light to the subject from first irradiation means;
a step of, when it is determined that the subject is wearing the glass or the like, applying light to the subject from second irradiation means, the second irradiation means being configured so that an angle between an optical axis of the light emitted from the second irradiation means and an optical axis of iris imaging means is larger than an angle between an optical axis of the light emitted from the first irradiation means and the optical axis of the iris imaging means, the iris imaging means being means for photographing an iris of the subject;
a step of operating a guiding means so that the subject is guided so as to move to an overlapping range between an irradiation range of the first irradiation means and an imaging range of the iris imaging means when it is determined that the subject is not wearing glasses or the like; and
a step of operates the guiding means so that the subject is guided so as to move to an overlapping range between an irradiation range of the second irradiation means and the imaging range of the iris imaging means when it is determined that the subject is wearing glasses or the like,
wherein the guiding means is a display, and
wherein an overlapping range between the irradiation range of the first irradiation means or the second irradiation means and the imaging range of the iris imaging means is highlighted on the display.

8. The imaging method according to claim 7,
wherein a direction in which the subject should move is indicated by an arrow on the display, and
wherein an instruction is displayed on the display.

9. The imaging method according to claim 7, further comprising:
a step of determining whether or not the glasses are a monocle when it is determined that the subject is wearing the glasses or the like; and
a step of controlling the second irradiation means so that light is emitted from the second irradiation means corresponding to an eye on which the monocle worn when it is determined that the glasses and like worn by the subject are the monocle.

* * * * *